(12) United States Patent
Genender et al.

(10) Patent No.: US 10,617,162 B2
(45) Date of Patent: Apr. 14, 2020

(54) GOWN WITH MOISTURE CONTACT INDICATOR

(71) Applicant: Medline Industries, Inc, Northfield, IL (US)

(72) Inventors: Alan Genender, Northbrook, IL (US); Audrey Putnam, Chicago, IL (US); Min Yao, Vernon Hills, IL (US)

(73) Assignee: Medline Industries, Inc., Northfield, IL (US)

(*) Notice: Subject to any disclaimer, the term of this patent is extended or adjusted under 35 U.S.C. 154(b) by 261 days.

(21) Appl. No.: 15/730,355

(22) Filed: Oct. 11, 2017

(65) Prior Publication Data

US 2019/0104779 A1 Apr. 11, 2019

(51) Int. Cl.
*A41D 13/12* (2006.01)
*A41D 13/00* (2006.01)
*A61F 13/00* (2006.01)

(52) U.S. Cl.
CPC ..... *A41D 13/1209* (2013.01); *A41D 13/0002* (2013.01); *A61F 13/00055* (2013.01)

(58) Field of Classification Search
CPC .............. A61F 13/00055; A41D 13/12; A41D 13/1209; A41D 13/1227; A41D 13/1236; A41D 13/1245; A41D 13/1263; A41D 13/1272; A41D 11/00; A41D 13/0002; A41D 13/04; A41D 13/1254; A41D 13/11; A41D 13/1281; A41D 31/00; A41D 31/02; A41D 31/04; A41D 31/10; A41D 31/125
USPC .......................... 2/114, 51; 116/206; 604/361
See application file for complete search history.

(56) References Cited

U.S. PATENT DOCUMENTS

| | | | | | |
|---|---|---|---|---|---|
| 2,156,880 | A | * | 5/1939 | Slomon .................. | A41D 27/00 116/207 |
| 2,214,354 | A | * | 9/1940 | Snelling ............... | G01N 31/222 116/206 |
| 3,317,283 | A | * | 5/1967 | King ..................... | G01M 3/042 422/421 |
| 3,675,654 | A | * | 7/1972 | Baker ..................... | A61F 13/42 604/361 |
| 3,731,685 | A | * | 5/1973 | Eidus ...................... | A61F 13/42 604/361 |
| 3,868,728 | A | * | 3/1975 | Krzewinski ........ | A41D 13/1227 2/114 |
| 4,231,370 | A | * | 11/1980 | Mroz ..................... | A61F 13/42 116/206 |
| 4,344,999 | A | * | 8/1982 | Gohlke .................. | A41D 31/02 128/849 |
| 5,435,010 | A | * | 7/1995 | May ........................ | A41D 7/00 116/206 |

(Continued)

OTHER PUBLICATIONS

Eric, "Luminescent Raincoat Lights Up the Rainy Days", Inventor provided screenshot; Unknown source; Published Nov. 17, 2008.

(Continued)

*Primary Examiner* — Amy Vanatta
(74) *Attorney, Agent, or Firm* — Philip H. Burrus, IV

(57) ABSTRACT

A gown (100) includes a body covering (101) disposed between a first sleeve (102) and a second sleeve (103). The body covering portion includes a first layer (106) coupled to a second layer (107) by an adhesive (108) comprising a unactivated colorant, such as an unactivated dye (109). The unactivated colorant transitions to an activated colorant (201) when wet, and the second layer absorbs the activated colorant.

20 Claims, 6 Drawing Sheets

(56) References Cited

U.S. PATENT DOCUMENTS

| | | | | |
|---|---|---|---|---|
| 5,897,541 | A * | 4/1999 | Uitenbroek | A61F 13/15203 604/358 |
| 6,559,351 | B1 * | 5/2003 | Eakin | A61L 15/56 602/41 |
| 6,653,522 | B1 * | 11/2003 | Blumenthal | A61F 13/42 604/361 |
| 2004/0191118 | A1 * | 9/2004 | Mody | G01N 31/222 422/401 |
| 2005/0234415 | A1 * | 10/2005 | Liu | A61F 13/42 604/361 |
| 2006/0143767 | A1 * | 7/2006 | Yang | A41D 19/015 2/16 |
| 2010/0012017 | A1 * | 1/2010 | Miller | A61B 5/015 116/201 |
| 2010/0119561 | A1 * | 5/2010 | Spindler | A61K 8/02 424/401 |
| 2015/0272495 | A1 * | 10/2015 | Greener | A61B 5/443 600/306 |
| 2016/0178603 | A1 * | 6/2016 | Patmore | G01N 21/8803 436/149 |
| 2017/0143553 | A1 * | 5/2017 | Bogue | A61F 13/00055 |

OTHER PUBLICATIONS

Brucker-Cohen, "Interview with Elise Co", Gizmodo Gallery: Elise Co; See Puddle Jumper (Co, 2000); https://gizmodo.com/196926/gizmodo-gallery-elise-co; Published Aug. 28, 2006.

* cited by examiner

GOWN WITH MOISTURE CONTACT INDICATOR

BACKGROUND

Technical Field

This disclosure relates generally to gowns, and more particularly to body covering gowns.

Background Art

Medical professionals frequently interact with various fluids, waste matter, and pathogens when rendering medical services. For example, when working in a decontamination area with medical instruments such as endoscopes, medical personnel may be exposed to high volumes of fluid. It is important to keep such fluids away from the skin, as such contact can result in the medical professional becoming infected or ill due to the microorganisms or pathogens present in the fluids.

One common technique to try and prevent fluids from contacting the skin is by donning a gown. Gowns can provide a protective function by helping to prevent the transmission of germs and microbes. Depending upon the material, gowns can further provide a protective function by preventing fluids, waste matter, and pathogens from contacting the skin of the wearer.

One problem with prior art gowns is that is not always clear whether microbes, germs, or other material has come into contact with the gown. It would be advantageous to have an improved gown.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
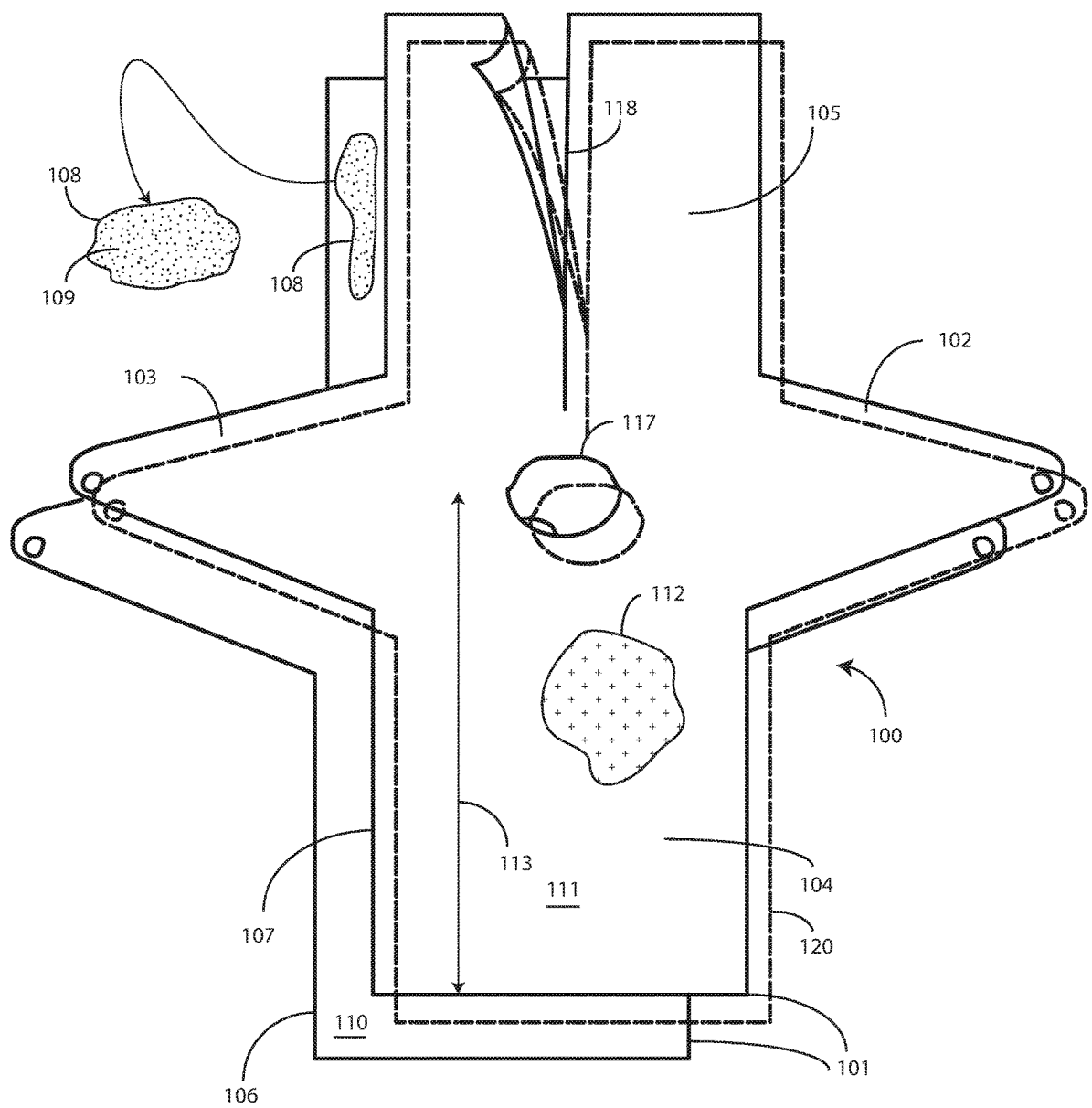
FIG. 1 illustrates one explanatory gown in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A.

Embodiments of the disclosure provide a gown that changes color when coming into contact with a liquid, such as water. In one or more embodiments, the gown includes an absorbent layer, an liquid impervious layer, and an activatable ingredient disposed between the absorbent layer and the liquid impervious layer. In one embodiment, the absorbent layer is the exterior layer of the gown, while the liquid impervious layer is the interior layer of the gown. In another embodiment, the reverse is true: the liquid impervious layer is the exterior layer of the gown, while the absorbent layer is the interior layer.

The activatable ingredient is a moisture indicator. In one or more embodiments, the moisture indicator can be a natural or synthetic dye. In other embodiments, the moisture indicator can comprise electronic sensors and output devices. Regardless of type, the moisture indicator is configured to change the color of the absorbent layer when the absorbent layer is contaminated with a liquid. Where the absorbent layer is the exterior layer, the activatable ingredient is activated when liquid-based contaminants contact the gown from the outside. By contrast, where the liquid impervious layer is the exterior layer, the active ingredient can be activated when the liquid impervious layer is damaged, i.e., when a "strike through" event occurs by which a liquid-based contaminant contacts the interior, absorbent layer.

In yet another embodiment, the gown comprises three layers. Illustrating by example, an absorbent layer can be disposed between two liquid impervious layers, with the activatable ingredient disposed between the absorbent layer and one or both of the two liquid absorbent layers. Where this is the case, the activatable ingredient is when either liquid impervious layer damaged by a "strike through" event and when a liquid-based contaminant contacts the interior, absorbent layer.

In one or more embodiments, a gown comprises a body covering. In one or more embodiments, the body covering comprises a first layer of material bonded to a second layer of material by an adhesive. In one or more embodiments, the adhesive comprises a coloring agent that, when coming into contact with a water-based liquid, turns a predefined color. In one or more embodiments, the colorant comprises an unactivated dye.

In one or more embodiments, the first layer of material defines an interior layer. The interior layer is so named because it is positioned toward a user when the gown is donned. In such an embodiment, the second layer of material defines an exterior layer. The exterior layer is so named because the first layer is disposed between the exterior layer and the user when the gown is donned.

To protect a user from coming in contact with liquids, pathogens, microbes, or other foreign materials, in one or more embodiments the first layer is liquid impervious. Illustrating by example, in one embodiment the first layer comprises a polyethylene film. Other materials suitable for use as the first layer of material will be described in more detail below. Still others will be obvious to those of ordinary skill in the art having the benefit of this disclosure.

In one or more embodiments, the second layer of material comprises a fabric. In one or more embodiments, the fabric is inorganic. For example, in one embodiment the second layer of material comprises a non-woven fabric of polypropylene. Other materials suitable for use as the second layer of material will be described in more detail below. Still others will be obvious to those of ordinary skill in the art having the benefit of this disclosure.

In one or more embodiments, the second layer of material is hydrophilic. This property causes the second layer of material to at least partially absorb liquids that come into contact with the second layer of material. The second layer of material can be configured to be hydrophilic in numerous ways. For instance, the method of manufacture can cause the material to absorb water. If the polypropylene is spunblown, for example, the resulting small fibers can trap liquid particles that contact the fabric. Alternatively, the material may be coated with a hydrophilic finish. For instance, the material may be coated with a water-attracting chemical. In one or more embodiments, this chemical is a surfactant. Other hydrophilic coatings suitable for use with embodiments described below will be obvious to those of ordinary skill in the art having the benefit of this disclosure.

In one or more embodiments, the unactivated dye is configured to change color when it becomes wet with a water-based liquid. For example, if blood, saliva, or other bodily fluids come into contact with the gown, in one or more embodiments the unactivated dye transitions to an activated dye. In one or more embodiments, this causes the gown to change color.

Illustrating by example, in one or more embodiments the unactivated dye is either clear or white. However, when this unactivated dye comes into contact with a water-based liquid, it transforms into an activated dye and takes on a predefined visible color. In one or more embodiments, the predefined visible color is a shade of red. Such a shade can be used when dry raspberry extract is used as the dye material.

Advantageously, when the gown comes into contact with a liquid, the unactivated dye transitions to an activated dye and is absorbed into the second layer of material. This causes the second layer of material to change color at locations contacted by the liquid. This alerts the user to the fact that the gown has come into contact with a liquid and may be contaminated. Accordingly, the user is advantageously alerted to the fact that the gown needs to be discarded and replaced. This prevents the user from wearing a contaminated gown into a procedure, thereby preventing the potential contamination of a patient or other person who may come into contact with the exterior of the gown.

Figure 6:
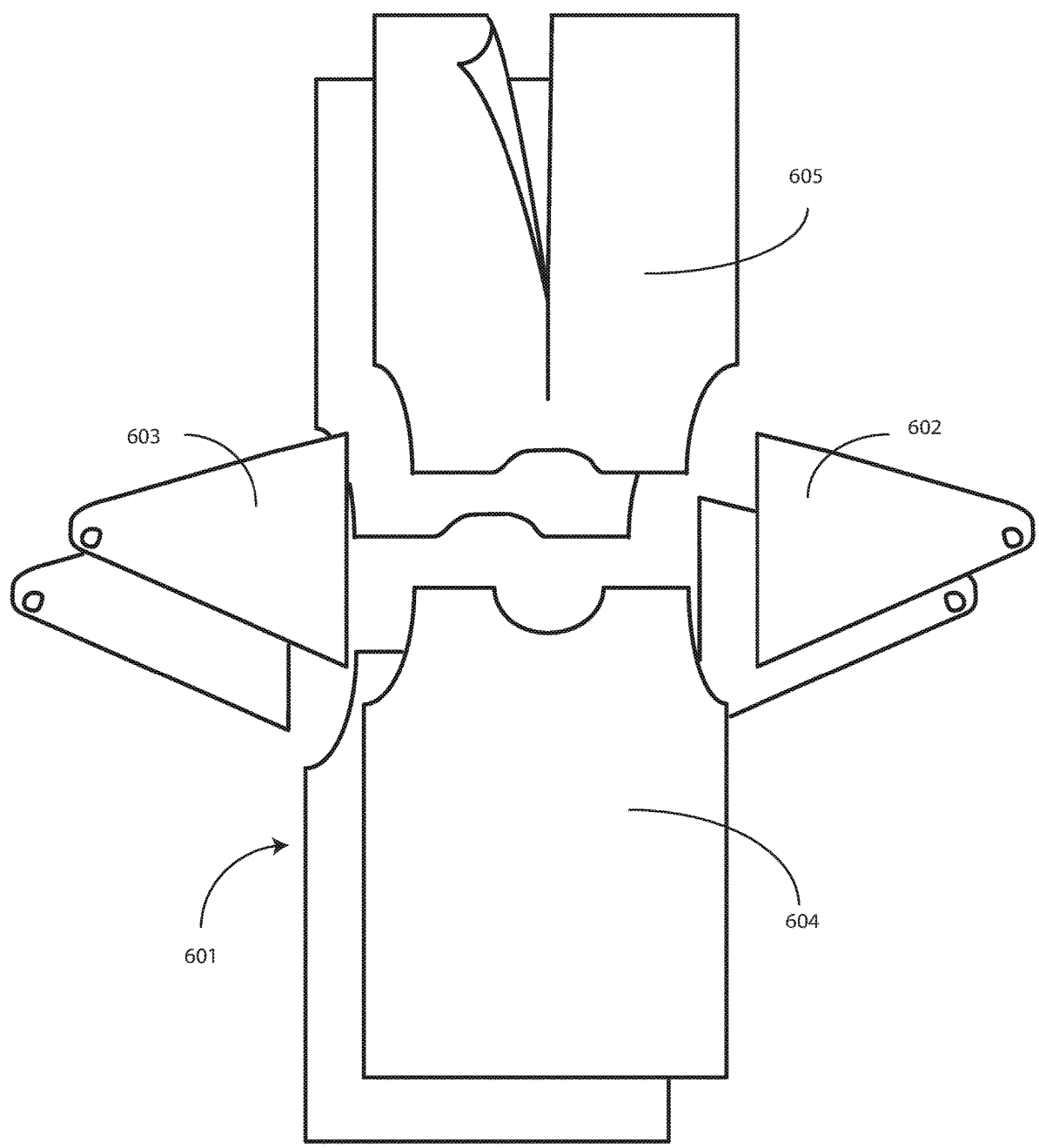
FIG. 6 illustrates another explanatory gown in accordance with one or more embodiments of the disclosure.

Turning now to FIG. 1, illustrated therein are components of one gown 100 configured in accordance with one or more embodiments of the invention. In one or more embodiments, these components include a body covering portion 101, a first sleeve 102, and a second sleeve 103. In this illustrative embodiment the body covering portion 101, the first sleeve 102, and the second sleeve 103 are configured as a single, continuous, unitary layer. However, in other embodiments, these components can be separated, as shown by the gown of FIG. 6. Turning briefly to FIG. 6, in other embodiments the first sleeve 602 and the second sleeve 603 can be separate components that are attached to the body covering portion 601. Similarly, the body covering portion 101 can be separated into a front body covering portion 604 and a rear body covering portion 605. The components are shown in FIGS. 1 and 6 as if cut from a template prior to each component being assembled to form a gown.

Turning now back to FIG. 1, in this illustrative embodiment the body covering portion 101 comprises a first layer 106 and a second layer 107. The first layer 106 is laminated or bonded to the second layer 107 by an adhesive 108 in one or more embodiments. It should be noted that the use of adhesive 108 is merely one way to bond the first layer 106 and the second layer 107. Other bonding methods include ultrasonic bonding, thermal bonding, mechanical bonding, and so forth. Still other techniques for laminating or bonding the first layer 106 to the second layer 107 will be obvious to those of ordinary skill in the art having the benefit of this disclosure.

As will be described in more detail below with reference to FIG. 2, in one or more embodiments the adhesive 108 comprises a moisture indicator. In one or more embodiments, the moisture indicator can be a natural or synthetic dye. In other embodiments, the moisture indicator can comprise electronic sensors and output devices. Regardless of type, the moisture indicator is configured to change the color of the absorbent layer when the absorbent layer is contaminated with a liquid. For illustration purposes, the moisture indicator will be described as an unactivated dye 109. However, other examples of moisture indicators are described above. Still others will be obvious to those of ordinary skill in the art having the benefit of this disclosure.

Continuing with the example of an unactivated dye 109 as the moisture indicator, when in the unactivated state, the unactivated dye 109 has a first color, which can be clear, white, or another neutral color. However, in one or more embodiments, when the unactivated dye 109 comes into contact with a liquid, such as a water-based liquid, it transitions into an activated state to become an activated dye. When in the activated state, the activated dye takes on a predefined visible color such as red, blue, or green. In one embodiment, the unactivated dye 109 comprises dry raspberry extract. In such an embodiment, the activated dye 109 would take on the predefined visible color of red.

In one or more embodiments, the first layer of material 106 is liquid impervious. Illustrating by example, in one or more embodiments the first layer of material 106 comprises a polyethylene film 110. In one or more embodiments, the second layer of material 107 is manufactured from a non-woven fabric 111. In one or more embodiments, the second layer of material 107 is absorbent, which means that it absorbs liquids, and in particular water-based liquids. The non-woven fabric 111 is a disposable material in one or more embodiments. For instance, in one or more embodiments, the second layer of material 107 comprises a polypropylene fabric.

In one or more embodiments, the first layer of material 106 functions as a water resistant lining that prevents the passage of fluids through one or more of the front body covering portion 104, the rear body covering portion 105, the first sleeve 102, and the second sleeve 103. Illustrating by example, in one or more embodiments the first layer of material 106 is manufactured from a water-repellent or water-impermeable material and/or is coated with such a water-repellent or water impermeable material to prevent the passage of fluids. As noted above, polyethylene film is one material suited to perform such functions. Other suitable materials will be obvious to those of ordinary skill in the art having the benefit of this disclosure.

The second layer of material 107 can take a variety of forms. In one embodiment, the second layer of material 107 comprises a fabric. In another embodiment, the second layer of material 107 is not a fabric.

In one embodiment, the second layer of material 107 can be any type of absorbent material, as long as it is in an absorbent sheet format. Examples include water absorbent film, paper, and so forth.

In one or more embodiments, the second layer of material 107 can include various woven, non-woven, hydroentangled materials, and/or combinations thereof. Examples of materials suitable for use as the second layer of material 107 include absorbent Airlaid, spunlace, blends of polyester, polypropylene, polyethylene, urethane, and/or combinations thereof. The second layer of material 107 can be manufactured using various methods, including a spunbond metblown spundbond (SMS) method, a spunbond metblown metblown spunbond method (SMMS), and a spunbond metblown metblown spunbond method (SMMMS). In other embodiments, the second layer of material 107 is manufactured by weaving, knitting, needle punch, or a mixture of all of the above.

The second layer of material 107 may, or may not be, hydrophilic. For example, in one embodiment the second layer of material 107 simply has good water absorption properties. In one embodiment, the second layer of material 107 comprises a cotton based fabric having inherent water absorption properties. In another embodiment, the second layer of material 107 comprises hydrophilic fibers (water loving fibers, such as cotton, rayon, viscous, tencel, silk, etc), or super absorbent fibers.

In still other embodiments, the second layer of material 107 is designed to be hydrophilic. This property causes the second layer of material 107 to at least partially absorb liquids that come into contact with the second layer of material 107.

The second layer of material 107 can be configured to be hydrophilic in numerous ways. For instance, the method of manufacture can cause the second layer of material 107 to absorb liquids, and in particular water-based liquids. Where, for example, the second layer of material comprises non-woven polypropylene strands that are manufactured using an SMS process, the resulting small fibers can trap liquid particles that contact the fabric.

In other embodiments, the second layer of material 107 is coated with a hydrophilic finish 112. For instance, the second layer of material 107 may be coated with a water-attracting chemical as the hydrophilic finish 112. In one or more embodiments, this chemical is a surfactant. Other hydrophilic finish 112 coating suitable for use with embodiments described below will be obvious to those of ordinary skill in the art having the benefit of this disclosure.

While various materials suitable for use as the first layer of material 106 and the second layer of material 107 have been described, numerous other fabrics suitable for either layer will be obvious to those of ordinary skill in the art having the benefit of this disclosure. For example, in another embodiment the first layer of material 106 can be manufactured from polypropylene. In still another embodiment, the first layer of material 106 can be manufactured from Tyvek™. Similarly, the second layer of material 107 can be manufactured from another non-woven material, which may be organic or inorganic, such as a cotton, polyester, or a cotton polyester blend. Additionally, one or more antimicrobial layers can be added to either of the first layer of material 106 or the second layer of material 107 in one or more embodiments to enhance antimicrobial protection.

In one embodiment, the first layer of material 106 comprises the exterior layer of the gown 100, while the second layer of material 107 comprises the interior layer of the gown 100. In another embodiment, the first layer of material 106 comprises the interior layer of the gown 100, while the second layer of material 107 comprises the exterior of the gown.

In still another embodiment, a third layer of material 120 is included. In one or more embodiments, the third layer of material 120 is liquid impervious. Illustrating by example, in one or more embodiments the third layer of material 120 comprises a polyethylene film. In one or more embodiments, the third layer of material 120 functions as a water resistant lining that prevents the passage of fluids therethrough.

In such an embodiment, the first layer of material 106 and the third layer of material 120 are disposed on either side of the second layer of material 107. Accordingly, the first layer of material 106 and the third layer of material 120 define the interior and exterior of the gown 100, respectively. In other embodiments, the third layer of material 120 will be omitted.

In one embodiment, regardless of whether two layers of material or three are used, the length 113 of the gown 100 is configured to run from a wearer's shoulder to below their knee. The length 113 of the gown 100 is configured to run from the wearer's shoulder to a location along their mid-calf. In yet another embodiment, the length 113 of the gown 100 extends from a wearer's shoulder to their feet. Other lengths will be obvious to those of ordinary skill in the art having the benefit of this disclosure.

In one embodiment, the gown 100 may optionally include pockets or other surface features, none of which is shown in FIG. 1 for simplicity, but that will be obvious to those of ordinary skill in the art having the benefit of this disclosure.

The gown 100 may be manufactured in various colors. As the second layer of material 107 is the exterior layer of the gown 100, it frequently defines the color. Exceptions occur in cases where the second layer of material 107 is partially translucent, where a combination of the color of the first layer of material 106 and the second layer of material 107 will define the color of the gown 100.

In one or more embodiments where the gown 100 is used in medical applications, the gown 100 is manufactured so as to be white. Accordingly, in one or more embodiments at least the second layer of material 107 is white. Moreover, in one or more embodiments the first layer of material 106 is also configured to be white. In other embodiments, the gown 100 can be blue or yellow. Yellow is a color particularly well suited for medical procedures due to its high visibility and easy differentiation from a person's skin.

In one or more embodiments, the front body covering portion 104 is configured as a frontal body covering portion in that it is configured to cover the frontal portion of some or all of a user's body, or in another embodiment the frontal portion of some or all of a user's torso, when the user is wearing the gown 100. The rear body covering portion 105 is configured to cover at least some of the rear portion of some or all of a user's body, or in another embodiment the rear portion of some or all of a user's torso, when the user is wearing the gown 100.

In the illustrative example of FIG. 1, the front body covering portion 104 and the rear body covering portion 105 have a substantially similar length 113. In other embodiments, the length of the front body covering portion 104 and the rear body covering portion 105 will be different. In one embodiment for example, the front body covering portion 104 will be longer than the rear body covering portion 105, thereby covering more of the wearer's body in the front than the rear. In another embodiment, the front body covering portion 104 will be shorter than the rear body covering portion 105, thereby covering less of the wearer's body in the front than in the rear.

In one embodiment, body covering portion 101 defines a head insertion aperture 117. A user may insert their head through the head insertion aperture 117 when donning the gown.

The perimeter of the head insertion aperture 117 can take a variety of shapes. For example, the head insertion aperture 117 can have an angle-tapered flat contour, with two angular side edges radially interfacing with a substantially flat contour. By contrast, as shown in FIG. 1, the head insertion aperture 117 can also be round, resembling a circle or ellipse. The head insertion aperture 117 can be generally circular, egg-shaped, oval-shaped, pear-shaped, football-shaped, or the like. Still other shapes will be obvious to those of ordinary skill in the art having the benefit of this disclosure.

In one embodiment, one or both of the front body covering portion 104 or the rear body covering portion 105 can define an opening 118. In this illustrative embodiment, the rear body covering portion 105 comprises the opening 118, which is configured as a slit with two sides that abut when the opening 118 is closed by touching together. In this illustrative embodiment, the front body covering portion 104 of the gown 100 is configured to be placed against the front of the torso of a wearer. The rear body covering portion 105 then covers the rear of the torso of the wearer and terminates at the opening 118.

The opening 118 in this embodiment has a left side and a right side, and is configured as an abutting, but openable, slit that runs most of the length 116 of the rear body covering portion 105, up the back of the gown 100. Said differently, the opening 118 extends from the base of the gown 100 toward, but not to, the head insertion aperture 117. As used herein, a "slit" means "a long, narrow cut or opening," in accordance with the plain, ordinary, English meaning as set forth in the New Oxford American Dictionary. It is not a gaping hole and does not include sides that do not abut when the opening 118 is closed.

The opening 118 can be used to assist in donning the gown 100. For instance, a user may open the opening 118 and pass their head, shoulders, and/or torso portions through the opening 118 when donning the gown. Said differently, the right side and left side of the opening 118 can be configured to permit the wearer to don the gown 100 by wrapping the right side and left side of the gown 100 about the wearer's torso.

The first sleeve 102 and the second sleeve 103 extend distally from the body covering portion 101 in this embodiment. The first sleeve 102 and the second sleeve 103 are configured to receive wearer's arms when the gown 100 is donned.

In the illustrated embodiment of FIG. 1, the first sleeve 102 and second sleeve 103 are illustrated as long sleeves. However, it will be clear to those of ordinary skill in the art having the benefit of disclosure that embodiments of the invention are not so limited. Gowns in accordance with embodiments of the disclosure may equally be configured with short sleeves or no sleeves has a particular application may warrant.

In one or more embodiments, the first sleeve 102 and the second sleeve 103 each terminate at a retention device configured to retain the first sleeve 102 and the second sleeve 103 to the arms of a wearer. In this illustrative embodiment, each retention device comprises a thumb loop. However, the retention devices can take other forms as well.

Illustrating by example, in other embodiments, the first sleeve 102 and the second sleeve 103 each terminate at a cuff. For instance, each of the first sleeve 102 and the second sleeve 103 can comprise knitted cuffs. In still other embodiments, each of the first sleeve 102 and the second sleeve 103 can terminate at drawstrings. In yet additional embodiments, each of the first sleeve 102 and the second sleeve 103 terminate at elastic gatherings. Other retention devices at which the first sleeve 102 and the second sleeve 103 terminate will be obvious to those of ordinary skill in the art having the benefit of this disclosure.

In one embodiment where a thumb loop is included, the thumb loop comprises a thumb insertion aperture through which a wearer's thumb may be inserted when the gown 100 is donned and the wearer's arms are inserted into the first sleeve 102 and the second sleeve 103, respectively. In one embodiment, each thumb loop is configured to engage the saddle of a thumb of a wearer. The thumb loops permit the heel of a wearer's hand to be exposed when the thumb is inserted into the thumb insertion aperture.

The thumb loops, where included, advantageously provide several functions. One illustrative function is that they keep the first sleeve 102 and the second sleeve 103 pulled along the wearer's arms so as to prevent the first sleeve 102 and the second sleeve 103 from "riding up" the arms of the wearer. Another illustrative function is that the thumb loops prevent twisting of the first sleeve 102 and the second sleeve 103 about the wearer's arm. Other advantages will be obvious to those of ordinary skill in the art having the benefit of this disclosure.

The base of either the front body covering portion 104 or the rear body covering portion 105 can take a variety of shapes. For example, in the illustrative embodiment of FIG. 1, the base is simply shown as being straight for ease of illustration. However, the base can take other shapes as well. For example, the base can substantially mirror the shape of the head insertion aperture 117. Other shapes will be obvious to those of ordinary skill in the art having the benefit of this disclosure.

In one or more embodiments, the gown 100 can include one or more tie members extending from the body covering portion 101. For example, the tie members include a first tie member extending from the left side of the gown 100 and a second tie member extending from the right side of the gown 100. Accordingly, one tie member can be disposed on one side of the opening 118, while the second tie member is disposed on a second side of the opening 118. Alternatively, the first tie member and second tie member can be attached to a common point on the gown as well.

Figure 2:
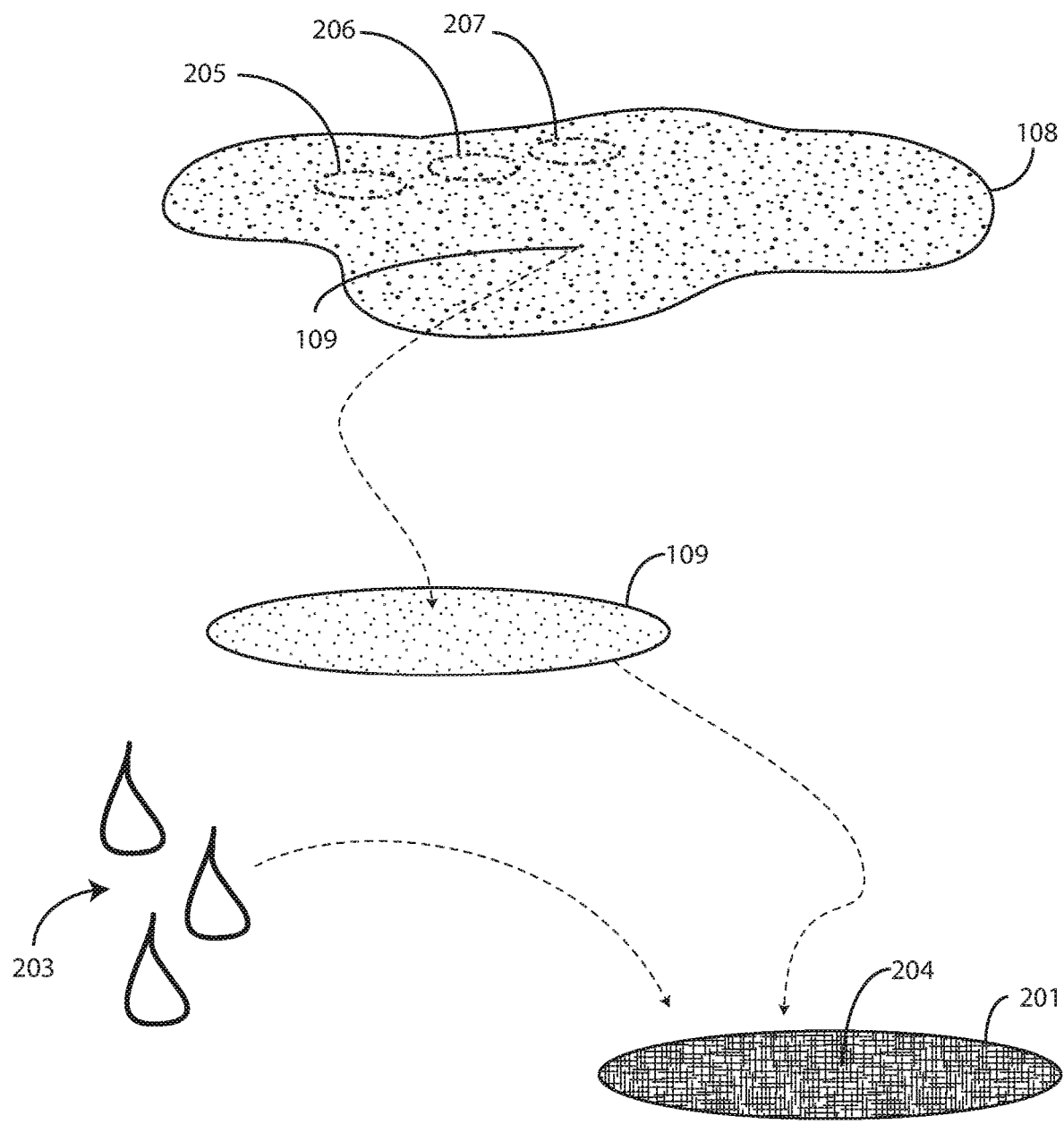
FIG. 2 illustrates one explanatory adhesive and dye or coloring agent in accordance with one or more embodiments of the disclosure.

Turning now to FIG. 2, illustrated therein is the adhesive 108 used to bond the first layer of material (106) to the second layer of material (107) and/or the third layer of material (120). In one or more an activatable ingredient is disposed between the second layer of material (107) and the first layer of material (106) and/or the third layer of material (120). The activatable ingredient, which can be a natural or synthetic dye, is configured to change the color of the absorbent layer, i.e., the second layer of material (107), when the absorbent layer, is contaminated with a liquid.

Where the absorbent layer is the exterior layer, the activatable ingredient is activated when liquid-based contaminants contact the gown from the outside. By contrast, where the liquid impervious layer is the exterior layer, the active ingredient can be activated when the liquid impervious layer is damaged, i.e., when a "strike through" event occurs by which a liquid-based contaminant contacts the interior, absorbent layer. When the gown comprises three layers, e.g., an absorbent layer disposed between two liquid impervious layers, the activatable ingredient is when either liquid impervious layer damaged by a "strike through" event and when a liquid-based contaminant contacts the interior, absorbent layer.

In one or more embodiments, the activatable ingredient comprises a natural or synthetic dye. This natural or synthetic dye can transition from an unactivated state to an activated state. Thus, prior to activation, in one or more embodiments the adhesive 108 comprises an unactivated dye 109.

In one or more embodiments, the adhesive 108 comprises a solvent-based glue. The use of a solvent-based glue means that water is not included as a constituent part of the adhesive 108. Accordingly, the glue will not transform the unactivated dye 109 into an activated dye 201.

In one or more embodiments, the unactivated dye 109 has a predefined appearance or color 202. The adhesive 108 can have the same predefined appearance or color 202 in some embodiments. In other embodiments, the adhesive 108 can have a different predefined appearance color than the unactivated dye 109. For example, in one or more embodiments, the adhesive 108 and the unactivated dye 109 are both clear. In another embodiment, the adhesive 108 is clear while the unactivated dye 109 is a dark color, such as blue or red. In another embodiment, the adhesive 108 is white while the unactivated dye 109 is a dark color. Other combinations will be obvious to those of ordinary skill in the art.

In one or more embodiments the second layer of material (107) of the gown (100) obscures the visibility of the unactivated dye 109. Illustrating by example, where the second layer of material (107) is white and the unactivated dye 109 is another color, the white color of the second layer of material (107) would prevent a user from seeing the unactivated dye 109 due to the fact that it is integrated into the adhesive 108 and is disposed behind the second layer of material (107). Accordingly, when the dye is unactivated, the gown (100) has a common color defined by the color of the second layer of material (107). This results in both the unactivated dye 109 and second layer of material (107) having a common appearance, i.e., the white of the second layer of material (107), despite the fact that each has a different individual appearance, due to the fact that the second layer of material (107) obscures the unactivated dye 109.

In one or more embodiments, when the unactivated dye 109 interacts with a liquid 203, such as water, it transitions to an activated dye 201. In one or more embodiments, the activated dye 201 is absorbed and dispersed by the second layer of material (107), much in the same way that a drop of ink is absorbed and dispersed by tissue paper. This results in the unactivated dye 109 becoming noticeably visible along the gown, with the predefined color 204 of the activated dye 201 being different from the predefined appearance or color of the second layer of material (107).

In one or more embodiments, the unactivated dye 109 comprises dry raspberry extract. Other examples of natural or synthesized water-actuated dyes will be obvious to those of ordinary skill in the art having the benefit of this disclosure. In one or more embodiments, when this dry raspberry extract comes into contact with a water-based liquid, it turns a predefined color 204, which is red. Since the second layer of material (107) is hydrophilic, in one or more embodiments it absorbs the activated dye 201. The second layer of material (107) also disperses the activated dye 201 in one or more embodiments. This causes the second layer of material (107) to turn red at locations where it is contacted by the liquid 203.

In one or more embodiments, this predefined color 204 is different from the color of the second layer of material (107). Advantageously, when the gown (100) comes into contact with a liquid 203, the unactivated dye 109 transitions to the activated dye 201 and is absorbed into the second layer of material (107). This causes the second layer of material (107) to change color at locations contacted by the liquid 203. This alerts the user to the fact that the gown (100) has come into contact with a liquid 203 and may be contaminated. Accordingly, the user is advantageously alerted to the fact that the gown (100) needs to be discarded and replaced. This prevents the user from wearing a contaminated gown into a procedure or around a patient, thereby preventing the potential contamination of a patient or other person who may come into contact with the exterior of the gown.

Additional components beyond the unactivated dye 109 can be added to the adhesive 108 in one or more embodiments. Illustrating by example, in one embodiment the adhesive 108 further comprises a super absorbent polymer 205. Where included, the super absorbent polymer 205 can trap the contaminating liquid within the adhesive to prevent further contamination.

In yet another embodiment, the adhesive 108 can comprise a super absorbent polymer 205 and an antimicrobial compound 206. Where included, the super absorbent polymer 205 can trap the liquid within the adhesive to prevent further contamination. The antimicrobial compound 206 can then disinfect the contaminants of the contaminating liquid.

In yet another embodiment, the adhesive 108 can comprise an antimicrobial compound 207 that is a dye itself. This can be included with or without a super absorbent polymer 205. One example of such an antimicrobial compound 207 is povidone-iodine powder.

Figure 3:
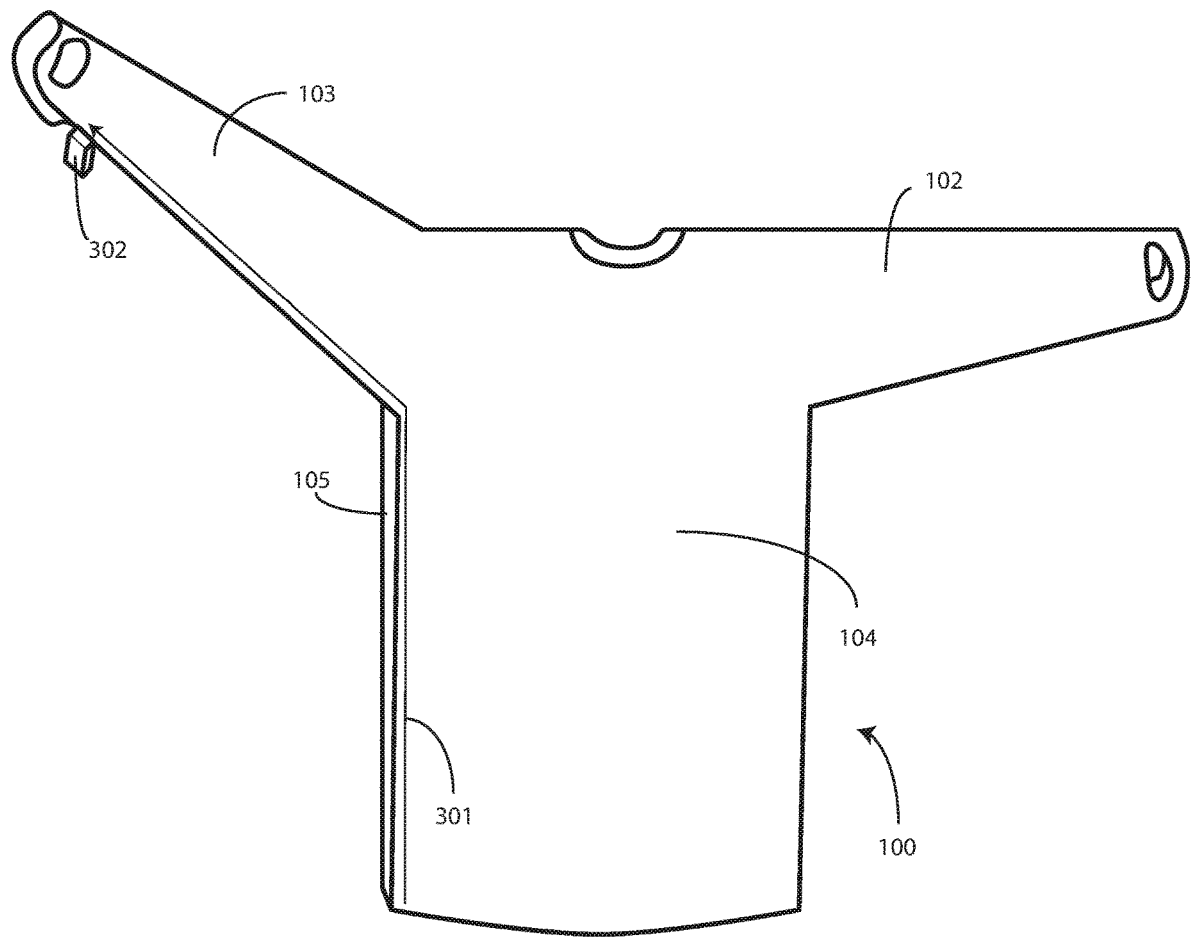
FIG. 3 illustrates one explanatory construction technique suitable for use with one or more gowns configured in accordance with one or more embodiments of the disclosure.

The gown (100) of FIG. 1 can be constructed in a variety of ways. One such example is shown in FIG. 3. Others will be obvious to those of ordinary skill in the art having the benefit of this disclosure.

Turning now to FIG. 3, seams 301 can seal edges of gown components with a thermal bonding device 302. Illustrating by example, the front body covering portion 104 is initially coupled to the rear body covering portion 105 by a thermal bonding device 302 that applies heat to each of the front body covering portion 104 and the rear body covering portion 105 by passing across portions of the front body covering portion 104 and the rear body covering portion 105. Said differently, in this illustrative embodiment the front body covering portion 104 and the rear body covering portion 105 are coupled together by thermal bonding.

However, as noted above, other coupling techniques can be used as well. Illustrating by example, in another embodiment the front body covering portion 104 and the rear body covering portion 105 are coupled together by adhesive bonding. In other embodiments, the front body covering portion 104 and the rear body covering portion 105 are coupled together by tape. Sonic welding, mechanical bonding, press-fit bonding, or other techniques can be used as well. Where the sleeves are separated from the front body covering portion 104 and the rear body covering portion 105, they can be attached thereto using these techniques as well.

The edges of the first sleeve 102 and the second sleeve 103 can be bonded using these techniques also. As shown in FIG. 3, a first edge of the second sleeve 103 is bonded to a second edge of the second sleeve 103 using the thermal bonding device 302. In one or more embodiments, both the front body covering portion 104 and the rear body covering portion 105, and the first edge of the second sleeve 103 and the second edge of the second sleeve 103 are bonded by a singular passage of the thermal bonding device 302 along each of the first edge of the front body covering portion 104 below the second sleeve 103, the second edge of the rear body covering portion 105 below the second sleeve 103, the first edge of the second sleeve 103, and the second edge of the second sleeve 103. This creates a continuous thermally bonded seam extending from a base of the gown 100 to a termination location on the second sleeve 103. The first sleeve 102 can be closed in similar fashion. The use of one, singular passage of the thermal bonding device 302 upon the underarm junction of the gown 100 provides a more robust, durable, and strong junction than when multiple passes are made across this location.

Figure 4:
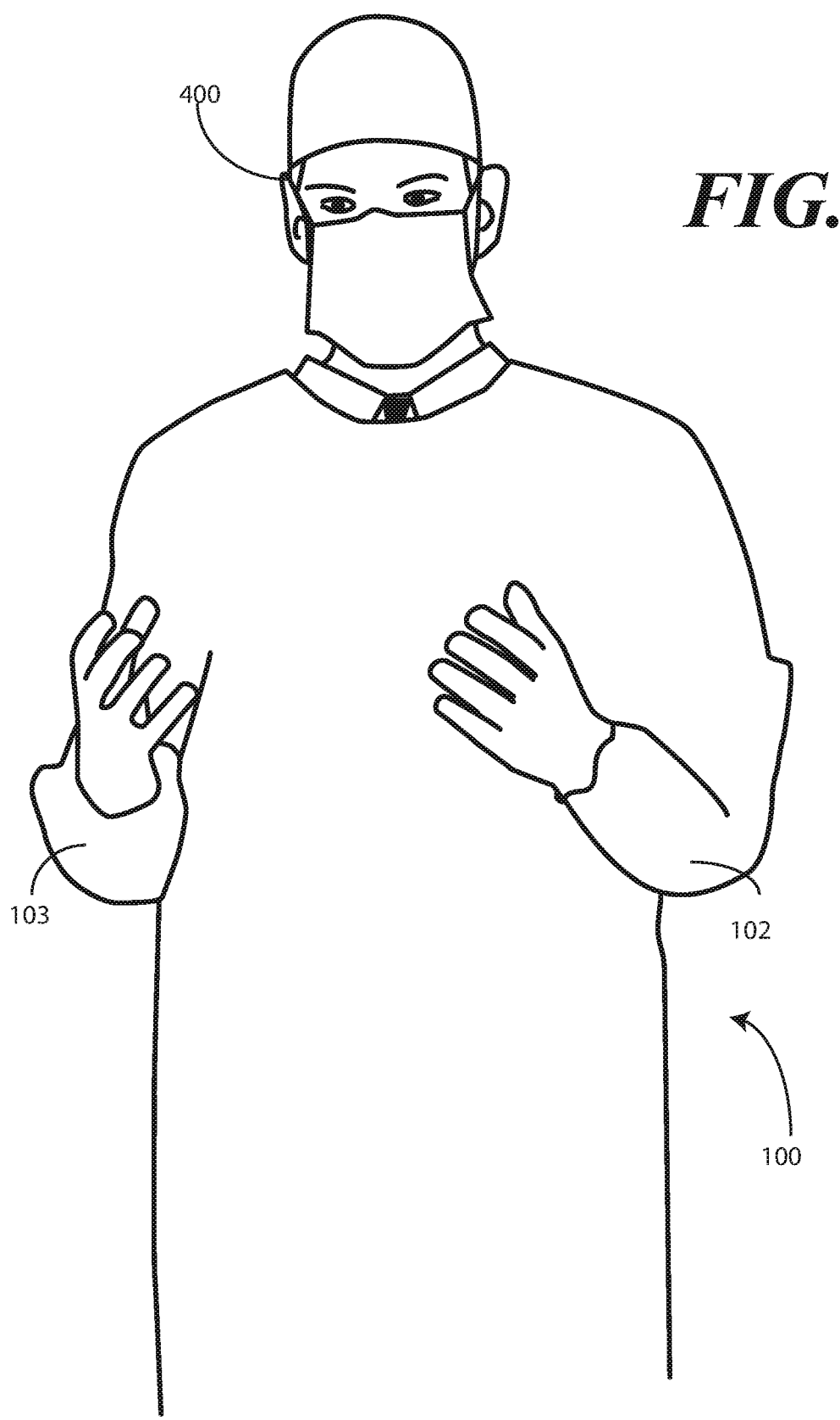
FIG. 4 illustrates a user wearing one explanatory gown configured in accordance with one or more embodiments of the disclosure, where a dye or colorant is in an unactivated state.

The resulting gown 100 is shown in FIG. 4 being worn by a user 400. As previously described, the gown 100 includes the body covering portion 101, which is disposed between the first sleeve 102 and the second sleeve 103. The body covering portion 101 includes the first layer (106), which in this embodiment is white, and the second layer 107, which in this embodiment is also white. An adhesive (108) comprising unactivated colorant (109) couples the first layer (106) to the second layer 107.

The second layer of material 107 is visible, and the colorant is in its unactivated state. To wit, the unactivated dye (109) is in the form of a fine powder and is integrated with the adhesive (108) disposed beneath the second layer of material. Accordingly, it cannot be seen.

Figure 5:
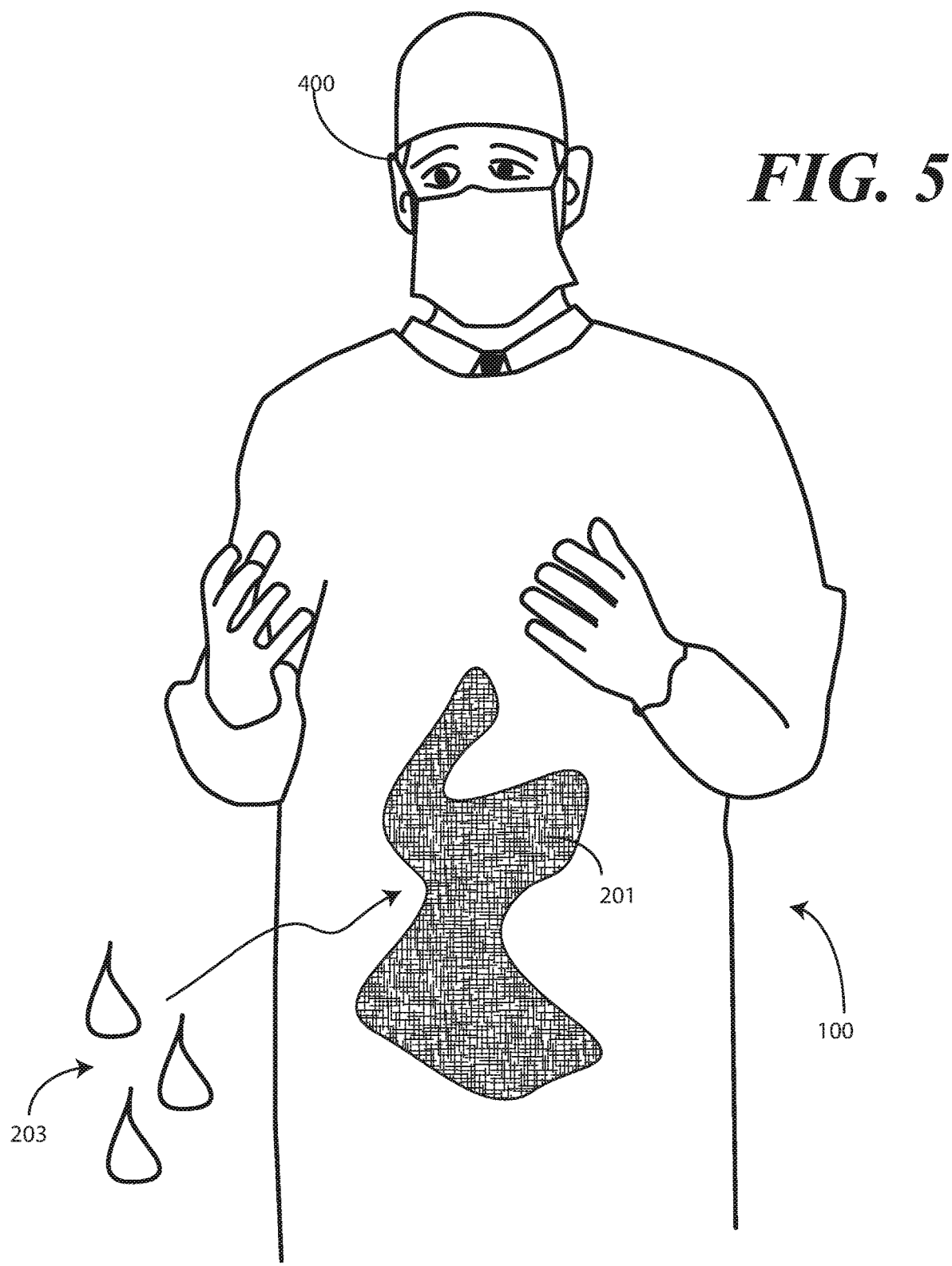
FIG. 5 illustrates the user wearing one explanatory gown configured in accordance with one or more embodiments of the disclosure where the dye or colorant is in an activated state.

Turning to FIG. 5, a liquid 203 has come into contact with the gown 100. Accordingly, the unactivated colorant (109) has transitioned to an activated colorant 201 due to the fact that it is wet. When this occurs, in one or more embodiments the second layer of material 107 absorbs the activated colorant 201 when it is wet. The second layer of material 107 can disperse the activated colorant 201 as well.

Since the activated colorant 201 is red, which is a different color from the second layer of material 107, the former becomes immediately visible, thus alerting the user to the fact that the gown 100 has become contaminated. The user 400 is thus understands that the gown 100 should be discarded and replaced before performing future procedures.

Accordingly, as shown and described above, a gown includes a colorant integrated into, and held fast by, an adhesive. The adhesive couples a liquid impervious layer, such as polyethylene film, to a non-woven layer such as spunbond polypropylene non-woven fabric. When the non-woven layer is exposed to a liquid, and in particular a water-based liquid, the colorant transitions to an activated state and is absorbed by non-woven layer, thereby causing the surface of the non-woven layer to turn a different color. This lets a wearer know they have been exposed to, and contacted by, a liquid.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims.

For example, as noted above, the use of an adhesive containing an unactivated dye as the activatable ingredient is only one embodiment. In other embodiments, the moisture indicator can be added to the absorbent layer through spraying. Alternatively, the moisture indicator can be mixed into the fiber of the absorbent layer during the forming process. The liquid impervious film surface can also be printed with the moisture indicator. Thus, the moisture indicator can be added to the absorbent layer or the liquid impervious film layer through other methods. Still other methods will be obvious to those of ordinary skill in the art having the benefit of this disclosure.

Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A gown, comprising:
   a body covering comprising a first layer of material bonded to a second layer of material by adhesive bonding with an adhesive;
   wherein:
   the adhesive comprises a moisture indicator;
   the moisture indicator comprises an unactivated dye that transitions to an activated dye upon contacting a liquid; and
   the second layer of material absorbs the activated dye from the adhesive upon the adhesive contacting the liquid.

2. The gown of claim 1, wherein the first layer of material is liquid impervious.

3. The gown of claim 2, wherein the second layer of material is hydrophilic.

4. The gown of claim 2, wherein the second layer of material comprises a hydrophilic surfactant.

5. The gown of claim 1, wherein the the unactivated dye and the adhesive have a different predefined appearance color.

6. The gown of claim 5, wherein the unactivated dye is darker in color than the adhesive.

7. The gown of claim 1, the second layer of material dispersing the activated dye in the second layer of material.

8. The gown of claim 6, wherein the activated dye is a predefined visible color.

9. The gown of claim 8, wherein the predefined visible color is different from another predefined color of the second layer of material.

10. The gown of claim 9, wherein the predefined visible color is red.

11. The gown of claim 10, wherein the unactivated dye comprises dry raspberry extract.

12. The gown of claim 6, wherein the first layer of material comprises a polyethylene film.

13. The gown of claim 12, wherein the second layer of material comprises a polypropylene fabric.

14. The gown of claim 13, wherein the first layer of material is bonded to the second layer by the adhesive, wherein the adhesive comprises a solvent-based adhesive.

15. A gown, comprising:
- a body covering disposed between a first sleeve and a second sleeve;
- the body covering comprising a first layer coupled to a second layer by an adhesive comprising an unactivated colorant;
- the unactivated colorant transitioning to an activated colorant when wet; and
- the second layer absorbing the activated colorant.

16. The gown of claim 15, the second layer obscuring visibility of the unactivated colorant.

17. The gown of claim 16, wherein the activated colorant and the second layer have different colors.

18. The gown of claim 17, wherein the second layer is white and the activated colorant is red.

19. The gown of claim 17, wherein the first layer comprises a polyethylene film and the second layer comprises a polypropylene fabric.

20. The gown of claim 19, wherein the polypropylene fabric is coated with a surfactant.

* * * * *